United States Patent
Ryan et al.

(10) Patent No.: US 7,361,513 B2
(45) Date of Patent: Apr. 22, 2008

(54) CELLULAR CONTROLS FOR GLYCATED HEMOGLOBIN HB A1C

(75) Inventors: Wayne L. Ryan, Omaha, NE (US); Jiong Wu, La Vista, NE (US)

(73) Assignee: Streck, Inc., La Vista, NE (US)

( * ) Notice: Subject to any disclaimer, the term of this patent is extended or adjusted under 35 U.S.C. 154(b) by 383 days.

(21) Appl. No.: 11/102,378

(22) Filed: Apr. 8, 2005

(65) Prior Publication Data
US 2006/0228803 A1    Oct. 12, 2006

(51) Int. Cl.
*G01N 33/72* (2006.01)
*G01N 33/50* (2006.01)

(52) U.S. Cl. .............. 436/67; 436/8; 436/15; 436/18; 436/63; 436/66; 436/174; 436/175; 252/408.1; 435/2

(58) Field of Classification Search .......... 436/8, 436/15, 18, 63, 66, 67, 174, 175; 252/408.1; 435/2
See application file for complete search history.

(56) References Cited

U.S. PATENT DOCUMENTS

| | | | | |
|---|---|---|---|---|
| 3,964,865 A | * | 6/1976 | Das | 436/66 |
| 3,973,913 A | * | 8/1976 | Louderback | 436/11 |
| 3,977,995 A | * | 8/1976 | Louderback et al. | 436/10 |
| 4,260,516 A | * | 4/1981 | Moore | 436/15 |
| 4,274,978 A | * | 6/1981 | Moore | 436/15 |
| 4,448,888 A | | 5/1984 | Bleile et al. | |
| 4,465,774 A | * | 8/1984 | Huang et al. | 436/15 |
| 4,590,164 A | * | 5/1986 | Gain | 436/15 |
| 5,132,230 A | * | 7/1992 | Rosenthal et al. | 436/15 |
| 5,589,393 A | | 12/1996 | Fiechtner et al. | |
| 5,919,708 A | * | 7/1999 | Sundrehagen | 436/66 |
| 6,162,645 A | | 12/2000 | Lee et al. | |
| 6,582,964 B1 | | 6/2003 | Samsoondar et al. | |
| 7,235,378 B2 | * | 6/2007 | Yonehara | 435/14 |
| 2003/0201177 A1 | | 10/2003 | Hodges et al. | |
| 2005/0175977 A1 | | 8/2005 | Posner et al. | |

FOREIGN PATENT DOCUMENTS

| | | |
|---|---|---|
| WO | WO 92/17107 | 10/1992 |
| WO | WO 92/22818 | 12/1992 |
| WO | WO 96/34290 | 10/1996 |

OTHER PUBLICATIONS

Cohen et al, "Purification of Glycated Hemoglobin", *Methods in Enzymology*, 231:65-75 (1994).
James M. Manning, "Preparation of Hemoglobin Derivatives Selectively or Randomly Modified at Amino Groups", *Methods in Enzymology*, 231:225-246 (1994).

* cited by examiner

*Primary Examiner*—Maureen M. Wallenhorst
(74) *Attorney, Agent, or Firm*—Howrey LLP

(57) ABSTRACT

Disclosed are cellular hemoglobin A1c (Hb A1c) normal and abnormal (high) controls for use in detecting Hb A1c levels. The present invention also relates to methods for generating cellular Hb A1c controls using red blood cells and methods for using the cellular controls. The present invention encompasses several methods for the preparation of Hb A1c cellular controls including: (1) a boronate method where the glycation occurs non-specifically; (2) a stabilized diabetic blood method where the glycation occurs specifically on Hb A1c, and (3) the glycation of normal blood method that is achieved by controlling conditions such that glycation occurs predominantly on Hb A1c. These methods produce cellular Hb A1c controls with desirable stability and that can be detected on a variety of instruments.

27 Claims, 7 Drawing Sheets

Typical Manufacturing Flowchart

Typical Manufacturing Flowchart

Slow Synthesis of Hb A1c

CELLULAR CONTROLS FOR GLYCATED HEMOGLOBIN HB A1C

BACKGROUND OF THE INVENTION

1. Field of the Invention

The invention relates to cellular controls for hemoglobin and, more specifically, to compositions and methods for generating suitable cellular, glycated hemoglobin A1c (Hb A1c) controls. In particular, cellular Hb A1c controls generated using a variety of methods are disclosed.

2. Description of Related Art

Hemoglobin (Hb) is a respiratory molecule found in red blood cells. It is responsible for transporting oxygen from the lungs to body cells and for transporting carbon dioxide from body cells to the lungs. Hemoglobin has a molecular weight of 64,000 Daltons and contains four polypeptide chains. Each chain binds to a heme group which consists of a tetrapyrrole ring chelated to an $Fe^{2+}$ ion. In the lungs, the iron atoms of the hemoglobin molecule reversibly combine with an oxygen molecule, which is then transported to body cells as blood circulates. The oxygen is released from the hemoglobin molecule in the tissues, and then the oxygen-free hemoglobin molecule picks up carbon dioxide, which is transported back to the lungs, where it is released.

Hemoglobin is produced from cells in the bone marrow that become red blood cells. Certain illnesses result in a deficiency of hemoglobin, such as anemia and sickle cell disease. Still other diseases, such as polycythemia or erythrocytosis, result in excessive levels of hemoglobin. Therefore, as an aid in the diagnosis or monitoring of such diseases, methods and devices for determining the concentration of hemoglobin in whole blood are valuable.

Hemoglobin may be modified by the free glucose present in human plasma to form glycated hemoglobin (GHB). Hemoglobin A1c (Hb A1c, also referred to as A1c), constituting approximately 80% of all glycated Hb, is generated by the spontaneous reaction of glucose with the N-terminal amino group of the Hb A beta chain. The Hb A1c and the total glycated Hb values have a high degree of correlation, and either value may be used, for example in the management of treating diabetes. Formation of Hb A1c is slow but irreversible, and the blood level depends on both the life span of the red blood cells (average 120 days) and the blood glucose concentration. Therefore, Hb A1c represents the time-averaged blood glucose values over the preceding 2 to 3 months, and is not subject to wide fluctuations observed in blood glucose values. With respect to diabetes management, studies have shown that quality of life improves with decreasing levels of Hb A1c, and measurements every 3 to 6 months are recommended.

The determination of total hemoglobin is indicative of the oxygen-carrying capacity of whole blood. An ability to measure hemoglobin in blood samples is an essential part of diagnostic analysis and is also important for monitoring responsiveness to therapies directed towards diseases that affect hemoglobin and to therapies that are directed towards other diseases but which may have adverse side effects on the hemoglobin level.

The numerous methods and devices for the determination of hemoglobin include both direct analysis, i.e., analysis without prior modification of the hemoglobin, and indirect analysis. An example of a direct analysis method is the Tallquist Method, wherein a measurement of the transmission or reflection optical density of the red color imparted by oxyhemoglobin, the natural form of hemoglobin, is obtained. An example of an indirect analysis method is the Drabkin's Method. In this method, the iron in hemoglobin is oxidized with a ferricyanide to form methemoglobin, which is converted with a cyanide molecule to cyanomethemoglobin, which is then measured spectrophotometrically. It is important to accurately determine the total hemoglobin in the Hb A1c assay, because A1c is often reported as a fraction of the total hemoglobin.

Multiple Hb A1c assay methodologies have been developed since late 1970s. One of the standard methods for measuring Hb A1c uses ionic-exchange high performance liquid chromatography (HPLC), which separates and analyzes Hb A1c and other minor Hb components from unmodified hemoglobin (Hb A0) based upon their differences in chemical charges. A second methodology for detection of Hb A1c is designed by immunoinhibition turbidimetric techniques. The HbA1c assay in immunoassay includes an antibody-antigen reaction and a following turbidity measurement. The third methodology is boronate affinity chromatography, which utilizes a gel matrix containing immobilized boronic acid to capture the cis-diol group of glycated hemoglobin. The variety of Hb A1c testing methodologies requires a novel control that could be used in various methods and devices for detecting Hb A1c levels.

In most of the available methods, the first step for measuring Hb A1c levels is the manual or automatic production of a hemolysate by lysing the red blood cells with a special lytic reagent. Therefore, there is an ongoing need for cellular Hb A1c standards or controls that exhibit a similar matrix to that of patient specimens and that function in the analytical testing phases during an Hb A1c assay.

Currently, there are a number of Hb A1c normal and abnormal controls on the market. Almost all of these hemoglobin A1c controls are in the form of protein powders (lyophilized) or hemolyzed liquid solutions. Although these A1c controls have been in the market for a long time, they have shown various limitations: (1) none of these controls provide information about RBC lysis, one of the required and critical QC steps; (2) the stability of the lyophilized controls upon rehydration (after the first use) is as short as 1-2 weeks, although the protein powders can be stored for long periods of time at −20° C.; and (3) none of the currently manufactured hemolyzed liquid controls can be applied to ionic exchange HPLC methods, the main method of Hb A1c testing. Thus, there is a need for cellular (whole cell, or mimics whole cells) and stable Hb A1c controls that can be used with all testing methodologies.

The present invention relates to developing normal and abnormal high cellular Hb A1c controls that have the following advantages over previous controls: (1) they will work with at least the current Hb A1c detection methodologies and systems; (2) in certain embodiments they will have an Hb A1c value of about 10% or higher for the abnormal high (Level II) control; (3) in certain embodiments they will be substantially intact erythrocytes and have at least about 3 to 12 months of stability; and (4) they will mimic the whole blood sample. In contrast to the short stability of the protein solution exhibited by rehydrated lyophilized controls, the cellular Hb A1c controls of the present invention (also referred to as being cellular, whole cell, or in-cell) will have a much longer stability period (at least from about 3-12 months) and will be easy to use. On the other hand, in contrast to the hemolyzed nature and limited usage of hemolyzed liquid controls, the cellular Hb A1c controls, containing intact RBCs, will be able to provide a complete control for the foreseeable QC steps and will be utilized for currently known and available testing methodologies.

SUMMARY OF THE INVENTION

The present invention relates to methods for generating cellular Hb A1c controls using red blood cells. Typically, mammalian red blood cells will be used in the present invention. The present invention encompasses several methods for the preparation of Hb A1c cellular controls including: (1) a unique method to stabilize Hb A1c and other hemoglobin fractions in RBC; (2) a method for preventing hemolysis of the red blood cells; (3) a method utilizing diabetic and normal whole blood to manufacture cellular A1c controls; (4) the glycation of normal blood method that is achieved by controlling conditions so that glycation occurs predominantly on the Hb A1c binding site of the normal blood; and (5) a cyanoborohydride glycation method where the fast glycation and pseudo-glycation occur non-specifically on normal, whole blood. These methods will produce cellular Hb A1c controls with desired stability that will be useful in a variety of testing systems.

Certain embodiments of the present invention provide a method for preparing a cellular hemoglobin A1c (Hb A1c) control using the following steps: (a) selecting a sample of red blood cells with at least one desired feature from a suitable subject; (b) washing the sample; (c) processing or filtering the washed sample to remove white blood cells; (d) preserving the Hb A1c molecules in said sample through a fixation procedure; (e) washing the sample of step (d); and (f) optionally adjusting the final Hb A1c level to a desired level thereby producing a cellular Hb A1c control, wherein the level of Hb A1c of the control is substantially stabilized and detectable. In certain embodiments, the method may also include a step of admixing the control of step (f) in a suspension medium suitable for delivering said control to a suitable detection device for analysis.

In certain methods, the sample is obtained from a mammal, an avian, or a reptile subject. In some embodiments, the sample is obtained from a human, or a bovine, or both human and bovine subjects. In other embodiments, the sample is obtained from a diabetic subject.

In certain embodiments, the Hb A1c level is detectable using immunologic detection, ion exchange, or affinity chromatography.

In additional embodiments, the Hb A1c level of the control is at least about 1-5%. In yet additional embodiments, the Hb A1c level of the control is greater than 5%.

In yet further embodiments, the Hb A1c level of the control is between about 5-20%.

In yet additional embodiments the preserving step of the method may include treating the cells with about 0.001-3% polyethylene glycol. In certain embodiments, the preserving step of the method may include treating the cells with about 0.001-4% glucose.

In some embodiments the method for preparing a cellular hemoglobin A1c (Hb A1c) control further includes in the preserving step, fixing the red blood cells. In some embodiments the fixing step may include treating the cells with from about 0.1-4 mL/L glutaraldehyde (25% stock).

In additional embodiments, the method for preparing a cellular hemoglobin A1c (Hb A1c) control further includes in the adjusting step, wherein the pH of the control is maintained at from about 6-8.

In yet additional embodiments, the method may include, after step (d) a step of incubating the red blood cells with about 0.001-6% glucose and about 0.001-6% $NaCNBH_3$ at room temperature or higher.

In other embodiments, the method may include-after step (c) a step of incubating the red blood cells for at least about 50 days, at about 4-6° C., with a glycation solution which comprises:
 0.04% Methyl paraben;
 0.3% PEG 20K;
 0.025% Inosine;
 0.015% Chloramphenicol
 0.04% Neomycin Sulfate
 0.585% EDTA ($2Na^+$);
 0.325% Magnesium gluconate;
 0.225% $Na_2HPO_4$;
 0.07% NaOH;
 0.005% NaF;
 3.15% Glucose wherein the osmolality of the glycation solution is adjusted to about 300±7 (mOsm) and pH is adjusted to about 7.0±0.1 in order to minimize the damage to RBC during the incubation. In certain embodiments, the incubation step will take place at about 6° C.

Embodiments of the present invention also include a cellular hematology control for Hb A1c comprising red blood cells having a desired level of Hb A1c and wherein the Hb A1c level is substantially stabilized.

Yet another embodiment of the present invention includes a cellular hematology control for Hb A1c prepared by a method using the following steps: (a) selecting a sample of red blood cells with at least one desired feature from a suitable subject; (b) washing the sample; (c) processing or filtering the washed sample to remove white blood cells; (d) preserving the Hb A1c molecules in said sample through a fixation procedure; (e) washing the sample of step (d); (f) optionally adjusting the final Hb A1c level to a desired level thereby producing a cellular Hb A1c control, wherein the level of Hb A1c of the control is substantially stabilized and detectable. In certain embodiments, the control maintains its Hb A1c level for at least about three months.

In other embodiments, the Hb A1c level of the control is at least about 1-5%. In yet other embodiments, the Hb A1c level of the control is greater than 5%. In yet additional embodiments, the Hb A1c level of the control is between about 5-20%.

In certain embodiments, the desired level of Hb A1c is substantially stabilized through adjusting the pH of the control to about 6-8.

In yet additional embodiments, the desired level of Hb A1c is substantially maintained through the addition of glucose to the control at an amount of from about 0.001-4%.

The term substantially stabilized encompasses situations where the Hb A1c level of the control varies by no more that about ±1-2%, and preferably, varies by no more than about 1% over time.

An additional embodiment of the present invention includes a method for determining the accuracy of a analytical instrument capable of measuring Hb A1c levels comprising the steps of:
a) providing a cellular HbA1c control of the present invention in a known reference quantity (e.g. an Hb A1c cellular standard); b) determining the level of Hb A1c in the control of step a with the instrument; and c) comparing the Hb A1c level obtained from step b with the known reference quantity; wherein the comparing indicates the accuracy of said hematology instrument. It will be desirable to obtain a value in step c that is within about 1-5% of the value of the known reference quantity. In certain embodiments, the Level I cellular Hb A1c controls of the present invention will serve as control or reference standard provided in a known reference quantity of step b, for the normal range of HbA1c levels (HbA1c levels less than or equal to about 6%) for use in a variety of diagnostic equipment, including in analytical instrument capable of measuring Hb A1c levels.

In additional embodiments, Level II controls having Hb A1c levels of greater than about 7%; and typically at a level between about 9-13% will be used as the cellular HbA1c control provided in a known reference quantity (e.g. a high Hb A1c cellular control or standard) of step b for use in a variety of diagnostic equipment, including in an analytical instrument capable of measuring Hb A1c levels. In these embodiments using the Level II controls, it will be desirable to obtain a value in step c that is within about 1-5% of the value of the known reference quantity.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
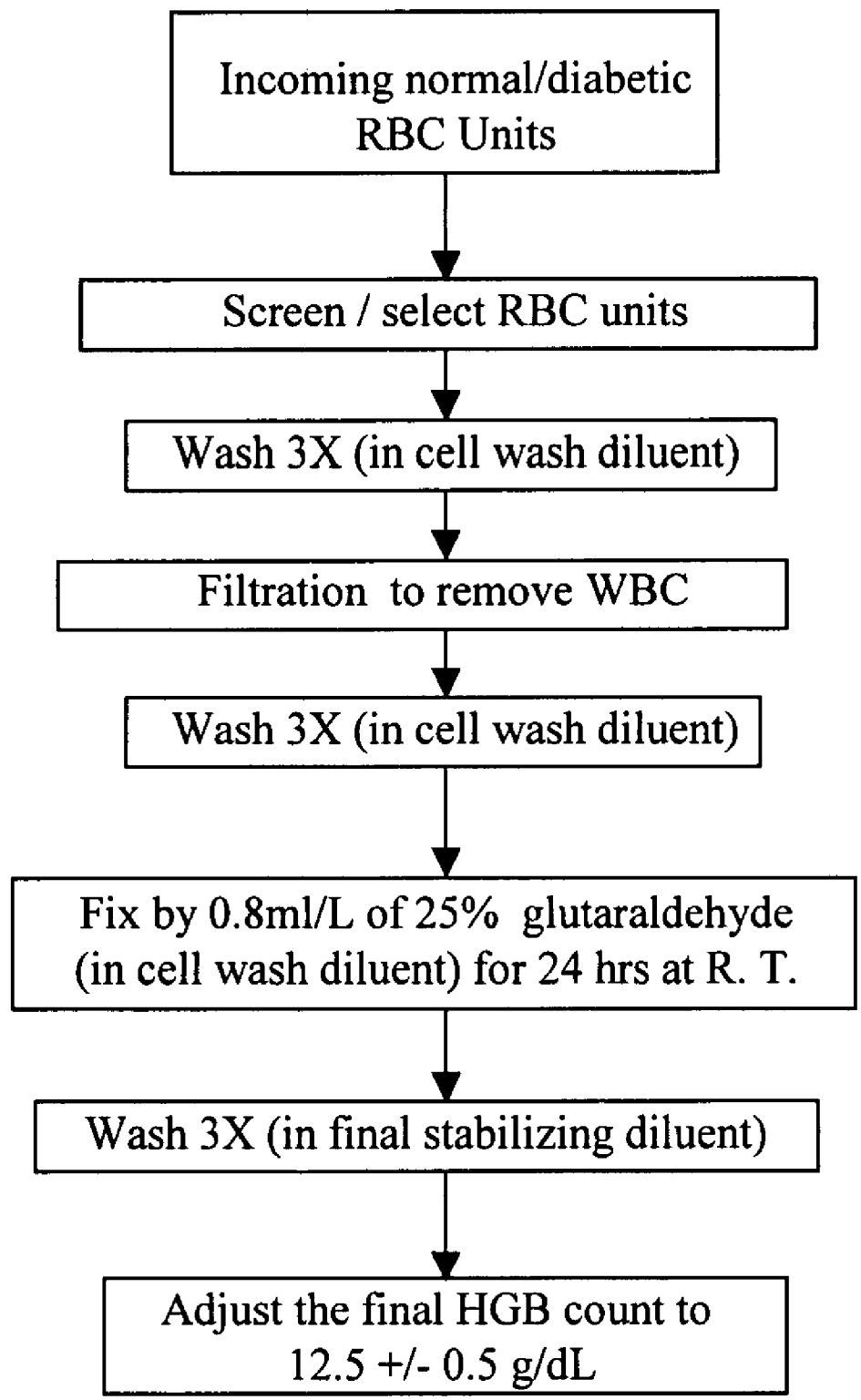
FIG. 1 is a flow chart of typical manufacturing steps for cellular Hb A1c controls.

The present invention overcomes the limitations of the prior art by providing stable, cellular Hb A1c normal and high controls. The present invention relates to developing normal cellular Hb A1c controls, and in certain preferred embodiments mammalian red blood cells are used as the sample source. Additionally, the present invention provides for abnormal high cellular Hb A1c controls using red blood cells. In some cases, the high cellular Hb A1c controls are prepared using red blood cells (RBC's) from diabetic donors as the sample source. These cellular or whole cell Hb A1c controls will exhibit desirable stability and will be useful in the major testing methodologies including immunoassay, ionic-exchange HPLC, and boronate affinity chromatography.

A. Use of Diabetic Donor Blood for Preparing High HbA1C Controls.

An embodiment of the present invention utilizes whole blood or RBC from diabetic donors as a sample source to generate Hb A1c controls. Healthy, (non-diabetic) people generally have Hb A1c levels of 4% to 6% (considered to be a "normal" Hb A1c level). In contrast, diabetic patients have higher percentages of Hb A1c, ranging from about 6% (in well-controlled diabetic patients) to greater than 15% (in poorly controlled diabetic patients). Thus, any Hb A1c level higher than about 6 or 7% is considered to be an abnormal high Hb A1c level.

The controls of the present invention have been divided into categories: Level I indicating controls with HbA1c levels of between about 4-7%; and Level II controls having Hb A1c levels of greater than about 7% or higher; and typically at a level between about 9-13%.

Current testing systems can accurately measure Hb A1c values from fresh whole blood samples (where fresh means that the samples have their original qualities unimpaired, or the samples are not decayed; typically, these are samples that are used within about 48 hours from blood drawing, but this time-frame can be longer, as long as the cells are not decayed). The term "whole blood" typically means unmodified (not separated), arterial or venous blood, such as that drawn from a subject. But the term is also intended to encompass any blood drawn from a subject that has not been separated into component parts by means such as centrifugation, and includes blood drawn into Vacutainer® tubes that may have certain additives, or preservatives for stabilizing the blood. There is an associated need for stable and easy to use Hb A1c controls or standards for calibrating these systems used to determine Hb A1c levels. Therefore, in one embodiment of the present invention, RBC's prepared from a diabetic patient having a higher than normal Hb A1c percentage are used as the raw material to produce a universal Hb A1c control product that would work on at least the current detection systems. Although there are other alternatives, such as slow synthesis (described in section D below), to prepare abnormal high A1c controls, the use of diabetic donor blood as raw material brings advantages during the manufacturing. The method described in this section minimizes the time required in sample preparation and prevents the undesirable non-specific glycation caused by the slow synthesis method.

B. Selection of Red Blood Cell Samples (1) Normal (Healthy) Units

Level I cellular Hb A1c controls were manufactured using qualifying red blood cells, as set forth below. The Level I cellular Hb A1c controls serve as standards for the normal range of HbA1c levels (HbA1c levels less than or equal to 6%) for use in a variety of diagnostic equipment. The qualifying normal red blood cell (RBC) units were used as the raw materials for manufacturing Level I cellular Hb A1c controls. The RBC units were purchased from a commercial blood bank. Each unit contained approximately 260 mL packed RBC (no plasma) and 60 mL Citrate, Phosphate, Dextrose, Adenine (CPDA) stabilizing solution. All RBC units were tested for HbsAg (non-reactive), HCV Ab (negative), HIV-2 Ab (negative), HIV-1 Ag (negative) and syphilis (negative) prior to shipment.

The qualifying RBC units were selected through a screening procedure. An ionic-exchange HPLC system was used to measure HbA1c for randomly selected RBC samples. The RBC units qualified for selection if they exhibited (1) $\leq 6\%$ A1c, (2) normal ranges of HbA1a ($\leq 1\%$), HbA1b ($\leq 1\%$), and Hb F ($\leq 1\%$), (3) lacked abnormal hemoglobin traits, such as S and C, (4) lacked visible clots, and (5) lacked significant amount of weak cells (often indicative of an abnormal level of hemolysis).

(2) Abnormal High (Diabetic) Units

Level II cellular Hb A1c controls were manufactured using RBC units that exhibited abnormal high Hb A1c levels ($\geq 9\%$). The abnormal high RBC units can be obtained and further validated from known diabetic donors. RBC units from 14 known diabetic donors were purchased from a commercial blood bank. However, the values of Hb A1c in these units varied significantly, ranging from 5% to >12%, from the diabetic RBC units. For this study, five RBC units were considered as "qualified" or "acceptable" for the present methods since their Hb A1c values were approximately 9% or higher. Thus, these units exhibiting Hb A1c values of about 9% or higher were further processed and used to manufacture the Level II cellular controls.

The RBC units with abnormal high A1c can also be achieved through large-scale "blind" or "flagged" screenings. A total of approximately 1400 "flagged" (donor's weight $\geq 180$ lbs) RBC samples were tested using a high-speed HPLC system in a span of eight weeks. The RBC units were selected as the raw material for manufacturing Level II controls if they exhibited (1) $\geq 9\%$ Hb A1c, (2) normal ranges of Hb A1a ($\leq 1.5\%$), Hb A1b (<1.5%) and Hb F ($\leq 1.5\%$), (3) lacked abnormal hemoglobin traits, such as S and C, (4) lacked visible clots, and (5) lacked significant amount of weak cells (indicative of abnormal levels of hemolysis). As a result, 37 of the 1400 "flagged" RBC units were found to be acceptable and used for manufacturing purpose, reflecting a qualification rate of 2.6%.

C. General Manufacturing Parameters for Cellular Hb A1c Controls (1) Cell Wash Diluent The cell wash diluent is used to replace plasma residues, as well as leukocytes and platelets, during the washing procedures. It contains appropriate cell stabilizers (e.g. magnesium gluconate, EDTA and PEG), cell metabolites (e.g. inosine and glucose), buffers (e.g. sodium phosphate dibasic and/or monobasic), antibiotics/antimicrobial agents (e.g. neomycin sulfate and chloramphenicol), and anti-fungal agents (e.g. methyl paraben). The diluent is neutral (pH=6.0-8.0) and isotonic or close-to-isotonic (osmolality=250-350 mOsm).

The selection of components and the concentration of each component in a given diluent are optimized to preserve each targeted cellular part. In particular, the diluents are responsible for minimizing or preventing cell swelling, shrinking, or hemolysis.

Certain Hb A1c preparations of the present invention utilize the cell wash diluent with the following general formulation:

TABLE 1

Cell Wash Diluent Components

| Components | Concentration (% w/V) |
|---|---|
| Polyethylene Glycol (FW: 200-50,000) | 0-3% |
| EDTA (disodium) | 0-3% |
| Magnesium Gluconate ($C_{12}H_{22}MgO_{14}.2H_2O$) | 0-1% |
| Sodium Phosphate dibasic ($Na_2HPO_4$) | 0-2% |
| Glucose | 0-4% |
| Methyl Paraben | 0-0.2% |
| Inosine | 0-0.2% |
| Neomycin Sulfate | 0-0.2% |
| Chloramphenicol | 0-0.2% |
| Sodium Hydroxide (NaOH) | 0-0.5% |
| Potassium Chloride (KCl) | 0-1.5% |
| pH (Final) | 6.0-8.0 |
| Osmolality (mOsm) | 250-350 |

The following is an example of the cell wash diluent that has been used to wash/stabilize red blood cell controls of the present invention.

TABLE 2

Cell Wash Diluent Example

| Components | Concentration (% w/V) |
|---|---|
| Polyethylene Glycol (FW: 20,000) | 0.70% |
| EDTA (disodium) | 0.70% |
| Magnesium Gluconate ($C_{12}H_{22}MgO_{14}.2H_2O$) | 0.39% |
| Sodium Phosphate dibasic ($Na_2HPO_4$) | 0.27% |
| Glucose | 0 |
| Methyl Paraben | 0.04% |
| Inosine | 0.025% |
| Neomycin Sulfate | 0.04% |
| Chloramphenicol | 0.015% |
| Sodium Hydroxide (NaOH) | 0.08% |
| Potassium Chloride (KCl) | 0.632% |
| pH (Final) | 7.0 |
| Osmolality (mOsm) | 300 |

(2) Cell Fixation Procedure

A cell fixation procedure using glutaraldehyde is performed between cell filtration and cell final wash. The fixation procedure serves to strengthen the cell membrane and to minimize the change in mean cell volume (MCV), thus to prevent the hemolysis of RBC. In addition, the fixation allows glutaraldehyde to cross link hemoglobin, which creates more homogeneity and stability of chemical charge for Hb and enhances its HPLC performance during the long-term stability test.

A general cell fixation procedure includes the following steps:

(2A) Adjust the count of filtered RBC to approximately 4±0.2 M/μL using the cell wash diluent described in Table 2. Measure the total volume of RBC.

(2B) Measure the same volume of cell wash diluent in another container. Add 0.1-4.0 mL/L of glutaraldehyde (25% stock) to the diluent and mix well.

(2C) Mix the RBC solution and glutaraldehyde solution thoroughly. Place the mixed solution at room temperature for 24 hours before final cell washing.

An example of the cell fixation procedure included the preparations of a 4.0 M/μL RBC solution and a 0.8 mL/L glutaraldehyde solution and a quick mixing of the two solutions at room temperature.

(3) Final Stabilizing Diluent

The final stabilizing diluent is used to stabilize the various controls of the present invention. It is desirable for the final stabilizing diluent to possess the following attributes: (1) to stabilize the value of % Hb A1c at both closed-vial and open-vial modes; (2) to prevent red blood cell hemolysis; and (3) to maintain the natural state of hemoglobin which allows higher quality of HPLC chromatograms.

Similar to the cell wash diluent, the final stabilizing diluent includes appropriate cell stabilizers (e.g. magnesium gluconate, EDTA and PEG), cell metabolites (e.g. inosine and glucose), buffers (e.g. sodium phosphate dibasic and/or monobasic), antibiotics/antimicrobial agents (e.g. neomycin sulfate and chloramphenicol), and anti-fungal agents (e.g. methyl paraben). In addition, final stabilizing diluent contains one or more of the following components: glucose, sodium fluoride and soybean trypsin inhibitor (SBI).

The formulations of final stabilizing diluents vary slightly depending upon the desired level of Hb A1c in the different levels of HbA1c controls (such as Level I or II). The final stabilizing diluent does not have to contain all of the components listed below, but will include at least as many of the below components to provide the desired, stabilized Hb A1c level. A general formula for the final stabilizing diluent includes the following components:

TABLE 3

Final Stabilizing Diluent Components

| Components | Concentration (% w/V) | |
|---|---|---|
| Polyethylene Glycol (FW: 200-50,000) | 0-3% | |
| EDTA (disodium) | 0-3% | |
| Magnesium Gluconate ($C_{12}H_{22}MgO_{14}.2H_2O$) | 0-1% | |
| Sodium Phosphate dibasic ($Na_2HPO_4$) | 0-2% | |
| Glucose | 0-4% | |
| Methyl Paraben | 0-0.2% | |
| Inosine | 0-0.2% | |
| Neomycin Sulfate | 0-0.2% | |
| Chloramphenicol | 0-0.2% | |
| Potassium Chloride (KCl) | 0-1.5% | |
| Soybean Trypsin Inhibitor (SBI) | 0-0.1% | (Final Addition) |
| Sodium Fluoride (NaF) | 0-0.5% | |
| Ciprofloxacin | 0-0.1% | (Final Addition) |
| Sodium Hydroxide (NaOH) | 0-0.5% | |
| pH (Final) | 6.0-8.0 | |
| Osmolality (mOsm) | 250-350 | |

An example of final diluent used for stabilizing a Level I control of the present invention includes the following components:

TABLE 4

Example Final Diluent For Stabilizing A Level I Control

| Components | Concentration (% w/V) | |
|---|---|---|
| Polyethylene Glycol (FW: 20,000) | 0.70% | |
| EDTA (disodium) | 1.17% | |
| Magnesium Gluconate ($C_{12}H_{22}MgO_{14}.2H_2O$) | 0.65% | |
| Sodium Phosphate dibasic ($Na_2HPO_4$) | 0.90% | |
| Glucose | 0.10% | |
| Methyl Paraben | 0.04% | |
| Inosine | 0.025% | |
| Neomycin Sulfate | 0.04% | |
| Chloramphenicol | 0.015% | |
| Soybean Trypsin Inhibitor (SBI) | 0.01% | (Final Addition) |
| Sodium Fluoride (NaF) | 0.005% | |
| Sodium Hydroxide (NaOH) | 0.11% | |
| pH (Final) | 6.90-7.10 | |
| Osmolality (mOsm) | ~300 | |

An example of final diluent for stabilizing Level II control includes the following components:

TABLE 5

Example Of Final Diluent For Stabilizing A Level II Control

| Components | Concentration (% w/V) | |
|---|---|---|
| Polyethylene Glycol (FW: 200-50,000) | 0.70% | |
| EDTA (disodium) | 1.17% | |
| Magnesium Gluconate ($C_{12}H_{22}MgO_{14}.2H_2O$) | 0.65% | |
| Sodium Phosphate dibasic ($Na_2HPO_4$) | 0.75% | |
| Glucose | 0.60% | |
| Methyl Paraben | 0.04% | |
| Inosine | 0.025% | |
| Neomycin Sulfate | 0.04% | |
| Chloramphenicol | 0.015% | |
| Soybean Trypsin Inhibitor (SBI) | 0.01% | (Final Addition) |
| Sodium Fluoride (NaF) | 0.005% | |
| Sodium Hydroxide (NaOH) | 0.11% | |
| pH (Final) | 6.90-7.10 | |
| Osmolality (mOsm) | ~300 | |

The stabilities of Hb A1c and RBC controls of the present invention are affected by a number of conditions and additives. In certain embodiments of the present invention, particularly Hb A1c/RBC stabilizers and/or stabilization procedures have been identified that enhance the overall performance of the controls of the present invention. Especially effective components in the final stabilizing diluent include glucose, sodium fluoride, and soybean trypsin inhibitor (SBI).

(5) Role of Glucose in the Final Stabilizing Diluent

Glucose provides a protective function in the final stabilizing diluent. The value of % Hb A1c tends to gradually decrease, up to 1 percentage point or more per month (at 6° C.), for untreated blood pool or improperly treated RBCs. This decrease in the Hb A1c measurements is likely to be due to a slight structural change in hemoglobin or a very slow release of glucose from glycated Hb under certain conditions.

The addition of glucose to the final stabilizing diluent of the Hb A1c controls provides continuous, although slow, glycation for hemoglobin that compensates for the gradual loss of Hb A1c over time. The optimal concentration of glucose depends on the initial starting level (Level I or II) of control and on the stability setup temperature. The optimal concentrations of glucose appeared to be about 0.1% and about 0.6%, respectively, for the Level I and II A1c controls at 6° C. The final stabilizing diluents disclosed in the Tables 4 and 5 above result in desired or optimum stabilities for both levels. The "desired or optimum stability" means essentially that the Hb A1c % of the control varies by no more that about ±1-5%, and preferably, varies by no more than about 1-2% over time, which may range from several weeks at room temperature, to at least several months, and in some cases greater than about 10 months or more at 6° C.

(6) Role of Sodium Fluoride in the Final Stabilizing Diluent

Sodium fluoride (NaF) exhibits multiple functions in Hb A1c stability studies. First, NaF in a glucose-containing diluent prevents glycolysis and helps to maintain an effective concentration of glucose. Therefore, NaF, along with glucose, serve to maintain the stability of the desired value of Hb A1c in controls of the present invention.

Fluoride is also believed to inhibit the intra-extra cellular ionic exchange for erythrocytes. The penetration of extra-cellular ions (e.g. $Na^+$ and $K^+$ to replace $H^+$) into red blood cells may result in charge alteration for hemoglobin, thus affect the HPLC readings of the Hb A1c controls. When added to controls of the present invention, NaF provides significant improvement to the Hb A1c controls of the present invention, resulting in less charge modification on Hb and less population of minor Hb components, Hb A1a, A1b and F.

Figure 4:
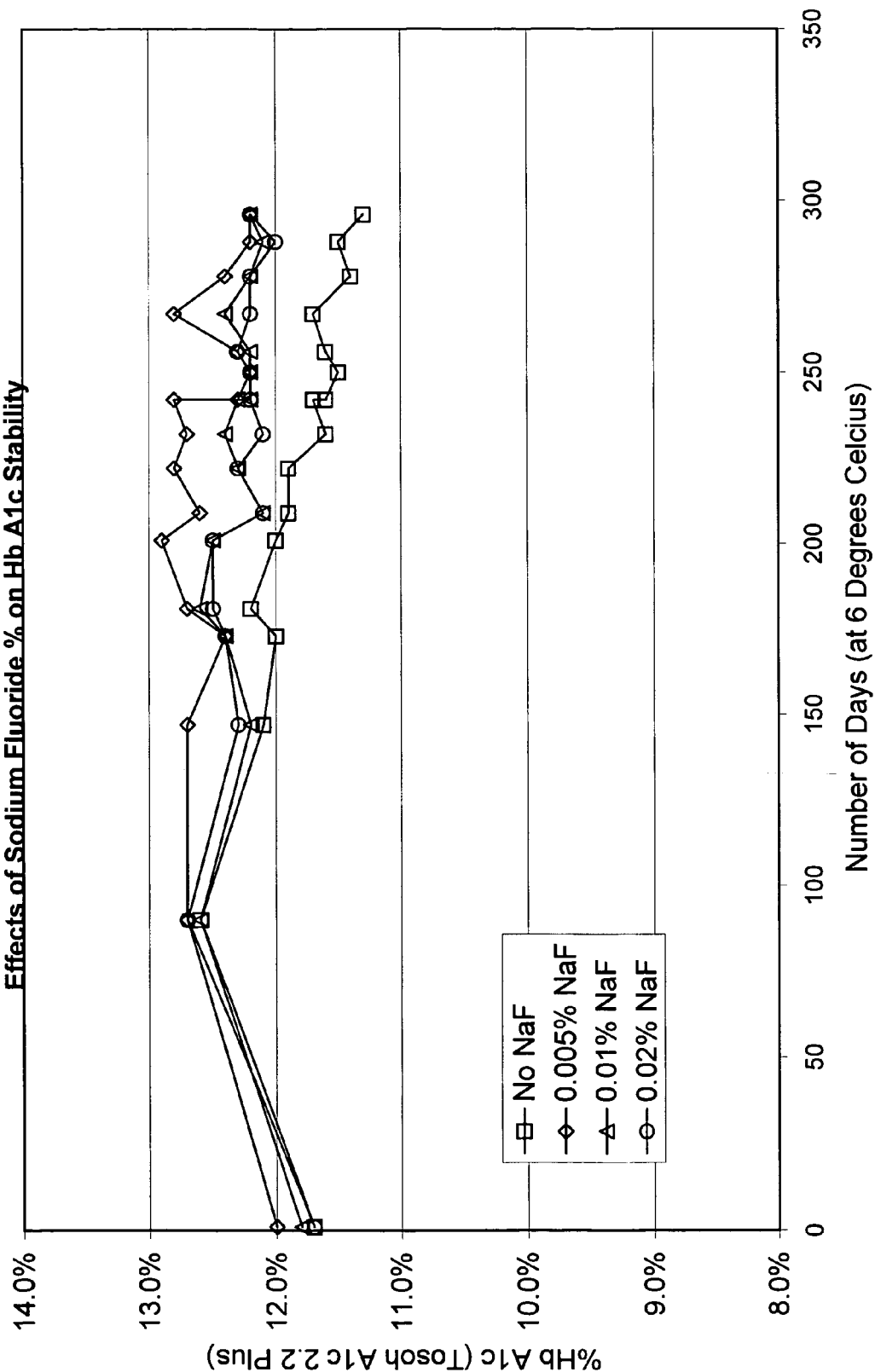
FIG. 4 shows the effects of sodium fluoride in preserving and stabilizing Hb A1c.
Figure 5:
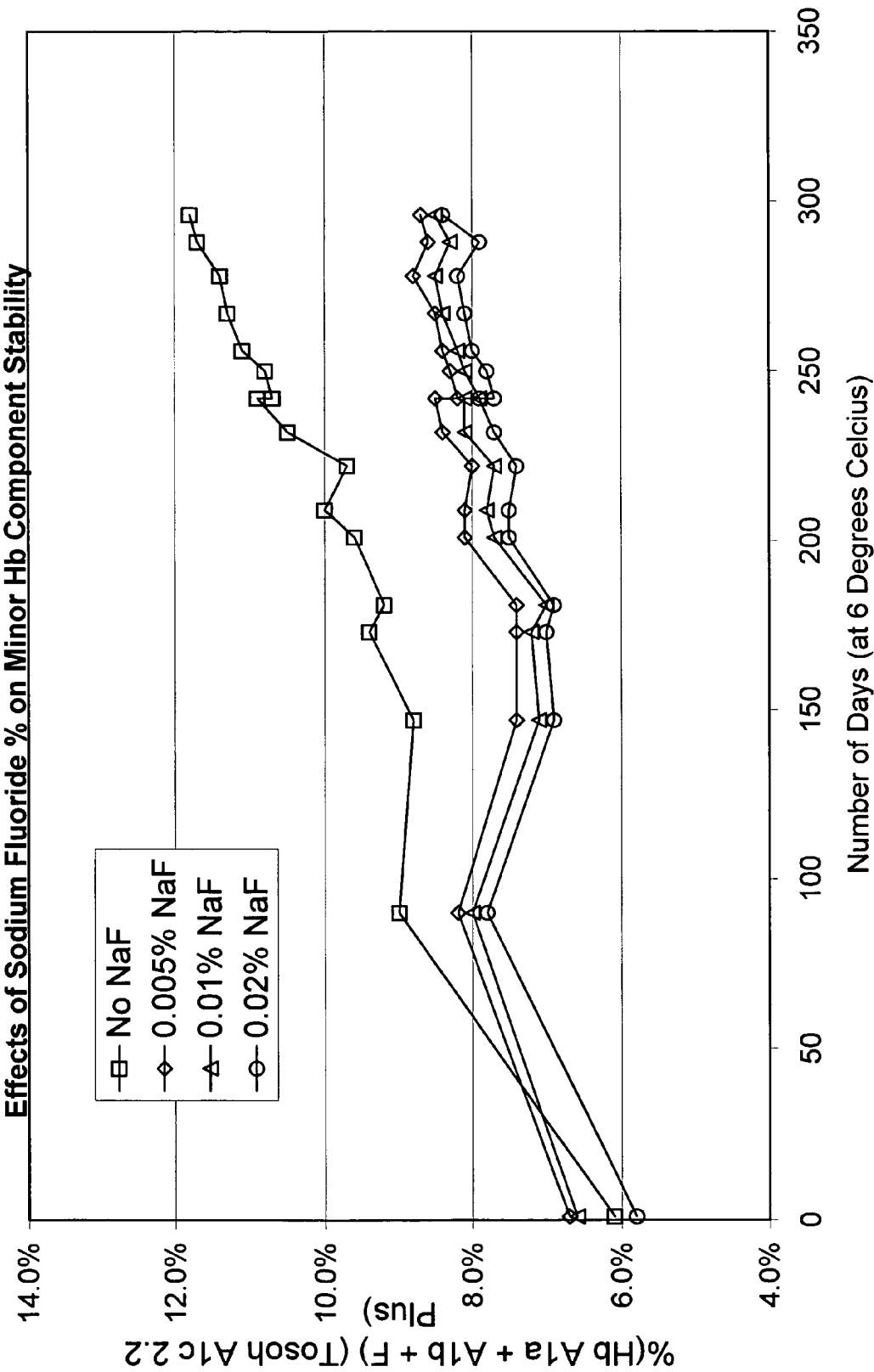
FIG. 5 shows the effects of sodium fluoride in preserving minor hemoglobin components.

The roles of NaF in the Hb A1c controls were investigated using four setups with a fixed glucose concentration ([Glucose]=0.8%) and various sodium fluoride concentrations ([NaF]=0, 0.005%, 0.01% and 0.02%). The net loss in % Hb A1c was 2.3% (percentage points, 11.7% vs. 9.4%) for the setup without NaF over 10 weeks at room temperature. In contrast, nearly no changes in % Hb A1c (−0.3% to −0.1%) were observed for the other three setups with NaF under the same experimental condition, as shown in FIG. 4. The three setups in the presence of NaF also showed improved HPLC chromatograms by minimizing the increase of Hb1a, A1b and F. The net increases were >10% and <5% (percentage points), respectively, for the NaF-free and NaF-containing setups, over 10 weeks at room temperature, as shown in FIG. 5.

(7) Soybean Trypsin Inhibitor

Soybean trypsin inhibitor (SBI) is known to block enzyme (protease) activity in order to strengthen cell membranes and prevent hemolysis. In studies utilizing controls of the present invention, 0.01% SBI was added from a 4% stock SBI solution to the final product (v/V=1:400). Although the addition of SBI did not affect the value of Hb A1c, it provided better stability for the control. In the presence of SBI, minimal hemolysis was observed for the cellular Hb A1c controls of the present invention, even after more than 100 days at room temperature, or more than 300 days at 6° C.

(8) Additional Effective Components/Factors

In addition to glucose, a suitable fluoride source, and soybean trypsin inhibitors, there are several additional components and/or factors that may provide slight improvements in the cellular Hb A1c controls of the present invention, including: EDTA, sodium phosphate dibasic and/or monobasic, and pH.

(9) Ineffective Components/Factors

Other components and/or factors have been tested in various studies. The following were found to be either ineffective or detrimental to the performance or stability of the cellular Hb A1c control products: lactose, mannitol, glyceraldehydes, procaine, adenosine, certain surfactants (such as SurModics® agents), bovine serum albumin, polylysine, doxycycline, and alternative fixatives such as diazolidinyl urea (DU), imidazolidinyl urea (IDU), and formaldehyde.

D. Generation of Hb A1c Controls Through a Direct Glycation Reaction.

Hemoglobin binds to glucose slowly in vivo to form glycated hemoglobin (GHB) through a two-step reaction.

(immunoassay, ionic-exchange HPLC, and boronate affinity) and have a desired, long stability.

The direct glycation features an incubation of unfixed red blood cells with approximately 6% A1c into a glucose-rich solution ([Glucose]=1-6%) at low temperature (about 6° C.). The glucose-rich solution, containing necessary cell stabilizers (e.g. magnesium gluconate, EDTA and PEG), cell metabolites (e.g. inosine), buffers (e.g. sodium phosphate dibasic and/or monobasic), antibiotics/antimicrobial agents (e.g. neomycin sulfate and chloramphenicol), and anti-fungal agents (e.g. methyl paraben), is isotonic (osmolality=250-350 mOsm) and has a neutral pH (pH=6-8).

Controls prepared using the direct glycation reaction showed very similar. values of Hb A1c percentages (9-10%), as determined by immuno-turbidity and ionic exchange assays, after about 7 weeks of direct glycation. However, controls tested using boronate affinity chromatography gave a higher derived value of Hb A1c (12-13%). This result is likely due to the additional non-A1c glycated hemoglobins that were also synthesized during the in vitro incubation.

Overall, the direct glycation reaction at low temperature, utilized in certain embodiments of the present invention, yielded about 2.5-3.0% Hb A1c and about 6.0% GHB. This reflected an approximate 40-50% glycation had occurred on the Hb A1c site. Using a higher temperature such as room temperature would generate less A1c and more non-A1c GHB and reduce that specificity to 10% or lower.

The direct glycation applies to the red blood cells with any level of Hb A1c. The incubation timeframe may range from 1 to 15 weeks in order to fulfill a satisfactory yield of Hb A1c and GHB. In addition, the yield of A1c and GHB is dependent on incubation temperature (with optimum tem-

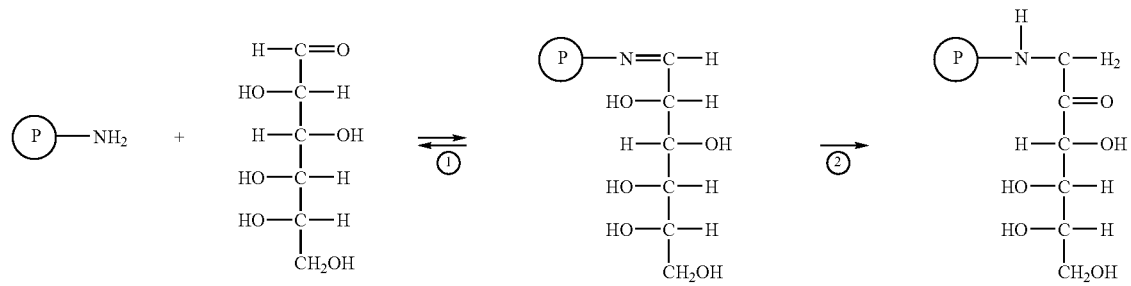

The step (1) is a fast and reversible step to yield a glycated intermediate,: Schiff base. The step (2) is an irreversible, though very slow, step to synthesize the final product through an Amadori rearrangement. The glycation may occur on the A1c binding site (Val 1 on the β chain) and other non-A1c sites (other Val and Lys residues). This slow binding suggests that a direct, but slow, glycation by incubating RBC in glucose-containing solutions is a possible route to improve the synthesis of hemoglobin A1c in vitro.

The present invention also embodies the manufacture and generation of abnormal high cellular Hb A1c controls through a direct glycation reaction (e.g. incubation of RBC in glucose-containing solutions). Inventive Hb A1c controls of the present invention generated by direct glycation are expected be useful in all of the major testing methodologies peratures ranging from about 1-15° C.), concentration of glucose, and other parameters of the glycation solution.

E. Glycation in the Presence of Sodium Cyanoborohydride (NaCNBH$_3$)

The cyanoborohydride method described below is designed for a specific Hb A1c assay methodology, boronate affinity chromatography.

Compared with other Hb A1c assay methodologies, the boronate affinity chromatography has been one of the newest and the most popular methodologies in the United States for the past ten years. In the affinity chromatography method, the gel matrix contains immobilized m-aminophenylboronic acid on the cross-linked, beaded agarose. The boronic acid reacts with the cis-diol groups bound to hemoglobin to form a complex, thus selectively holding the GHB on the column.

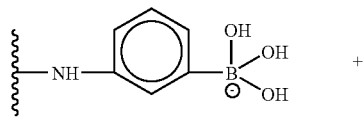

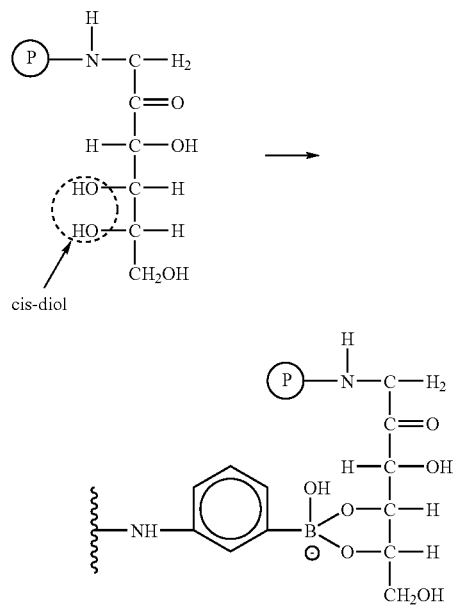

The non-GHB does not bind. Sorbitol is then added to dissociate the complex and elute the GHB. Absorbance (415 nm) of the bound and non-bound fractions is used to calculate the percentage of GHB, according to the equation shown below.

$$\%GHB = \frac{A(GHB) \times V(GHB)}{A(GHB) \times V(GHB) + A(non-GHB) \times V(non-GHB)}$$

In the above equation, A is the absorbance of GHB or non-GHB at 415 nm and V is the volume of the eluted hemoglobin fraction. The percentage of Hb A1c can be derived from an empirical formula: % Hb A1c=0.6846×% GHB+0.973258 (Little et al, *Clin. Chem.* 38, 2472-2478, 1992).

As described in Section D, it is possible to synthesize Hb A1c through a low temperature direct glycation process. However, such direct glycation usually takes weeks of incubation to achieve ideal yield. The unique design of the boronate affinity methodology allows both GHB and other pseudo-glycated proteins with the cis-diol group to be recognized as GHB during the measurement. Therefore, higher percentages of GHB can be achieved by an accelerated reductive glycation in the presence of sodium cyanoborohydride (NaCNBH$_3$):

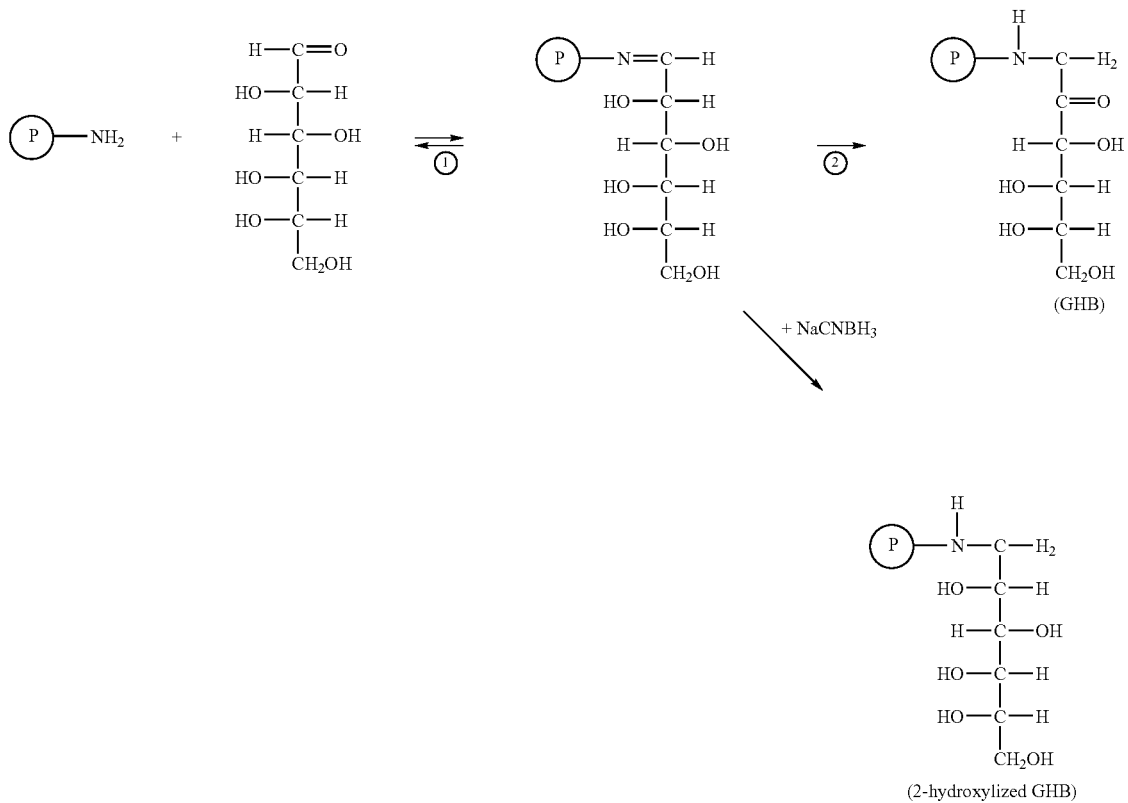

Using methods of the present invention, a significant amount (approximately 10% or more) of pseudo-GHB can be synthesized in erythrocytes within 24 hours. Like glycated hemoglobin, the stable pseudo-GHB contributes to the A1c reading using any boronate affinity based Hb A1c assay.

Prior to the synthesis, a glycation reaction solution containing 0.001-6.0% glucose and 0.001-6.0% NaCNBH$_3$ was prepared. The glycation reaction solution and packed normal RBC (unfixed) were then mixed at a 1:1 ratio. The mixture was incubated at 37° C. for 1 to 24 hours to accelerate the reaction. The values of GHB and Hb A1c were measured by various boronate affinity methods, such as Cholestech GDX® and Helena Laboratories® HbA1c kit. The yield of GHB/pseudo-GHB in this invention may be attributed to a few factors, including the concentrations of glucose and cyanoborohydride, reaction temperature, and reaction duration. The post-reaction RBC may be further washed and fixed for extended stability.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

Example 1

Preparing Abnormal High (Level II) Hemoglobin A1c Controls From Diabetic Donor Blood Samples (1) Donor Information All "flagged" RBC units as described in section D 2 above were purchased from a commercial blood bank. There were time intervals of 3 to 14 days between blood drawing and unit arrival. Each "flagged" unit, containing approximately 260 mL packed RBC and 60 mL Streck® CPDA diluent (described in section D 1), had been tested for HBsAg (non-reactive), HCV Ab (negative), HIV-2 Ab (negative), HIV-1 Ag (negative) and syphilis (negative) prior to the shipment. Qualified diabetic RBC units with abnormal high Hb A1c levels of a blood sample were identified through this "flagged" screening procedure using the Tosoh® A1c 2.2 Plus HPLC analyzer. Four of the qualified units were later used in the manufacture of Level II Hb A1c cellular controls. The data from the four qualified diabetic donor samples are summarized as follows:

TABLE 6

Information of Qualified Diabetic RBC Units

| No | Sex | Age | Weight (lb) | % Hb A1c (Tosoh A1c 2.2 Plus) |
|---|---|---|---|---|
| 1 | M | 35 | 188 | 12.8% |
| 2 | M | 53 | 250 | 10.6% |
| 3 | F | 48 | 187 | 12.7% |
| 4 | F | 64 | 231 | 13.1% |

(2) Manufacturing Abnormal High Hb A1c Controls

Aspects of the present invention include preserving the populations of Hb A1c and other hemoglobin components, preventing hemolysis of RBC, and producing cellular controls with desired stabilities. A typical manufacturing flowchart for preservation of Hb A1c and RBC for use in developing normal and abnormal high controls of the present invention is shown in FIG. 1. With regard to the procedures described herein, the composition and use of a cell wash and final stabilizing diluents, are especially useful for stabilizing the value of % Hb A1c, maintaining the natural state of Hb, and preserving the red blood cells manufactured in the present methods.

A Level II Hb A1c control (research pilot lot RPL #04140) was generated according to the above procedures described in Section C for stabilizing Hb A1c and preserving RBC. The four qualified RBC units were processed separately during the cell washing procedure and pooled together prior to the filtration step. Immediately following the completion of manufacturing process, the value of Hb A1c was measured at 12.0% using the Tosoh® A1c 2.2 Plus system, indicating no significant change in % A1c during the processing steps. Further review of the HPLC chromatogram revealed no significant change in the eluting pattern for a hemoglobin sample. The finished RPL product was filled into 12×76.5 mm plastic vials (for ionic-exchange HPLC methods) and 15×30 mm glass vials (for immunoassay and boronate affinity methods) before the stability tests (room temperature and 6° C.).

(3) Long-Term Stability of the RPL #04140 Level II Control

Figure 2:
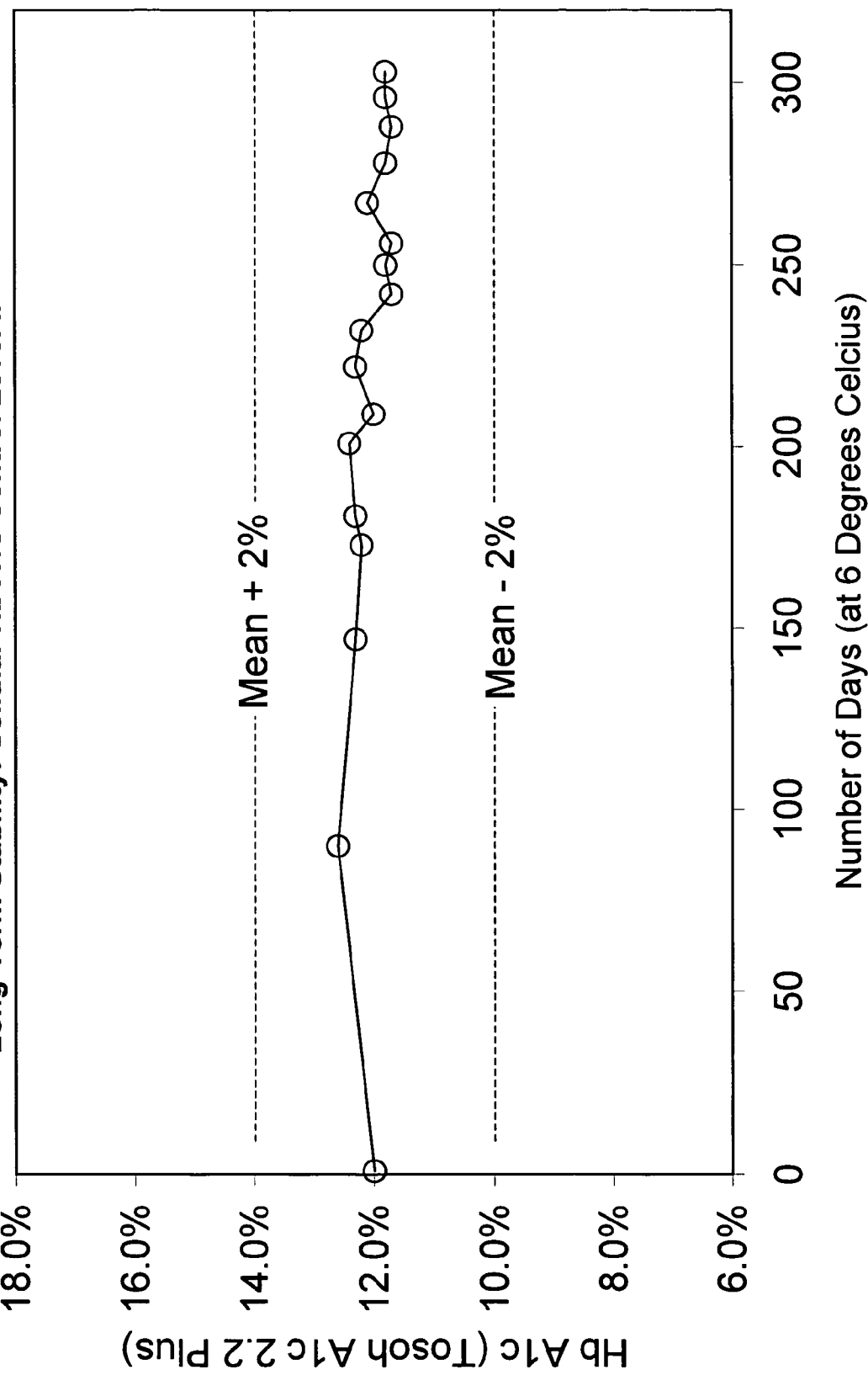
FIG. 2 shows the stability of the abnormal high (Level II) cellular Hb A1c control.

The long-term stability (LTS) tests demonstrate that (1) the abnormal high level Hb A1c varies no more than ±2% (percentage points), (2) minimal change in HPLC chromatogram, and (3) no/minimal RBC hemolysis, over the desired timeframe, which may range from several weeks at room temperature, to 10 months or more at 6° C. The stability of the Level II control was monitored using the Tosoh® A1c 2.2 Plus analyzer. FIG. 2 illustrates the stability plot for % Hb A1c. The values of % Hb A1c (12.0% and 11.8% for Day 0 and Day 303, respectively) remained nearly identical over a span of more than 300 days at 6° C. The changes in HPLC chromatograms, in terms of the values of other Hb components, were minimal during the same time span. No hemolysis was observed for the product at Day 303.

(4) Comparison of Hb A1c Values Using Various Testing Systems

The Level II Hb A1c control prepared from diabetic RBC units as described was also evaluated using a variety of other testing systems. The measured Hb A1c values were consistent using the instruments that employed all three major methodologies, as shown in Table 7 below:

TABLE 7

Hb A1c Values of the Level II Control (Multiple Analyzers)

| Testing System | Methodology | Hb A1c |
|---|---|---|
| Beckman ® CX/LX | Immunoassay | 12.3% (Day 301) |
| Bio-Rad ® Variant II | Ionic-Exchange HPLC | 12.4% (Day 295) |
| Cholestech GDX ® | Boronate Affinity | 13.3% (Day 301) |
| Tosoh ® A1c 2.2 Plus | Ionic-Exchange HPLC | 11.8% (Day 303) |
| Tosoh ® G7 | Ionic-Exchange HPLC | 12.5% (Day 295) |

(5) Parameters to Contribute to the Stability of Cellular A1c Controls

Additional studies investigated additional factors or parameters that might contribute to the stability of cellular Hb A1c controls. These parameters included varying diluent components, fixatives, and other chemicals present in the final product. Most of these parameters described below may also be suitable for the Level I control of the present invention.

(5A.) Glutaraldehyde Fixation

The Level II cellular Hb A1c control (previously described) was fixed by glutaraldehyde for 24 hours at room temperature. Pre-washed diabetic RBC at approximately $4 \times 10^6/\mu L$ (HGB=8-12 g/dL) was mixed with a 0.8 mL/L glutaraldehyde solution at an 1:1 ratio in the fixation procedure. The fixation step was intended to (1) strengthen the membrane of RBC to prevent/minimize hemolysis and (2) cross-link hemoglobin for stabilizing the chemical charges of Hb and achieving consistent HPLC performance.

Optimization of the level of fixation determined that using 0.8 ml/L of a 25% glutaraldehyde solution facilitated the best performance of cellular HbA1c controls. Weaker fixation tended to result in more hemolysis of RBC and less optimal HPLC chromatogram (e.g. unknown peaks in Tosoh® HPLC measurement) during the timeframe of stability tests. Stronger fixation, on the other hand, tends to cause false elevation in % Hb A1c value for some analyzers (e.g. Bio-Rad® Variant II).

(5B) Glucose

Figure 3:
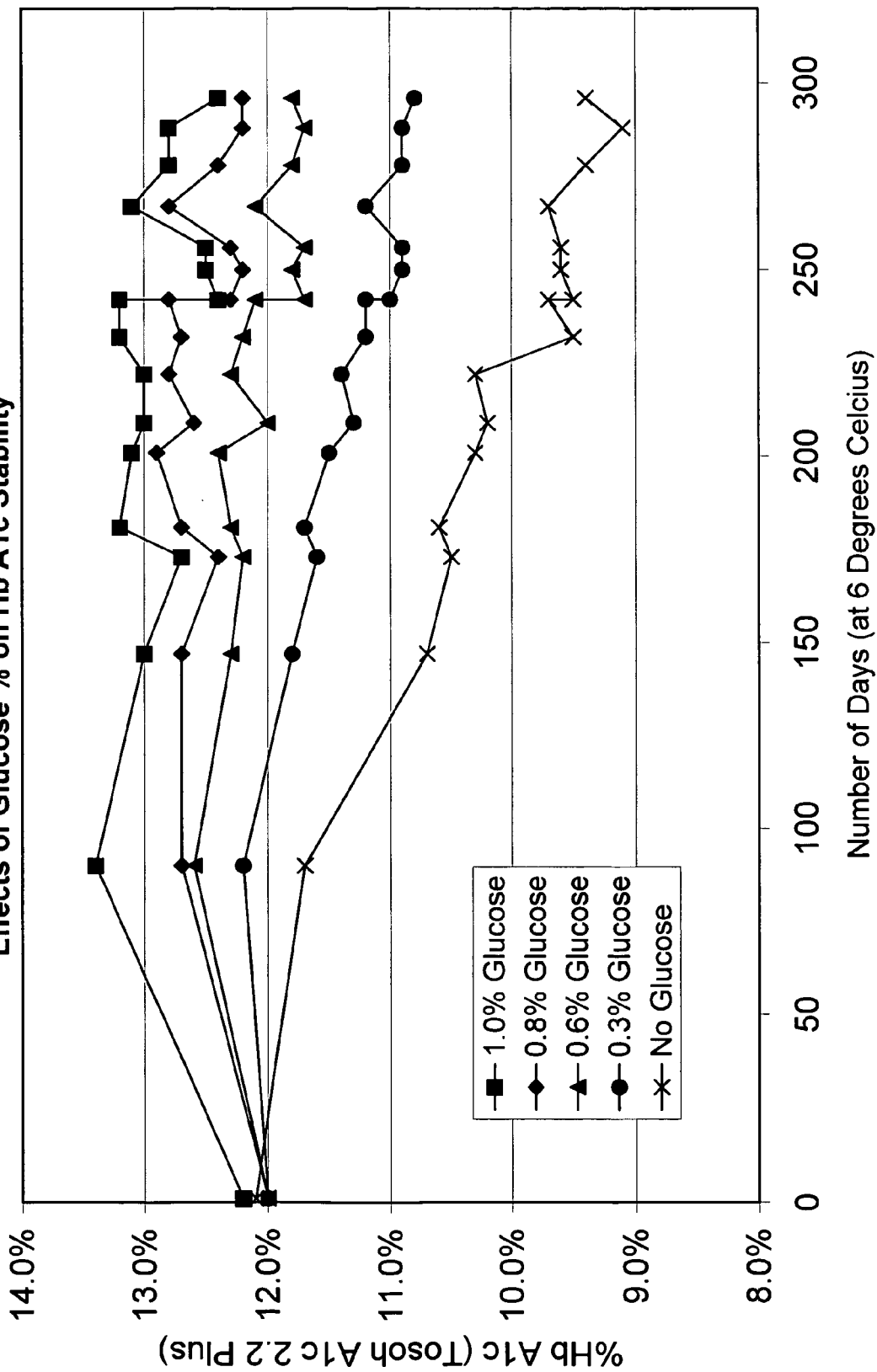
FIG. 3 shows the effects of glucose in preserving and stabilizing Hb A1c.

The optimal concentration of glucose used for the Level II control was approximately 0.6% (in the presence of 0.005% sodium fluoride). Glucose reacts slowly with unmodified Hb (Hb A0) to form Hb A1c and other glycated Hb, which compensates the slight loss of A1c (possibly due to the partial denaturing of protein) under the storage condition. Higher concentrations of glucose result in higher recovery of A1c values. FIG. 3 shows the correlation between the % Hb A1c stability and glucose concentration.

(5C) Sodium Fluoride

The optimal concentrations of sodium fluoride were 0.005% to 0.02% Sodium fluoride was added to prevent glycolysis of glucose in order to maintain a higher effective concentration of free glucose in the final product (FIG. 4) and to optimize the HPLC chromatograms by minimizing the increase in the presence of minor hemoglobin components, such as Hb A1a, A1b and F (FIG. 5). All four setups shown in FIGS. 4 and 5 contained 0.8% glucose in the final diluent as described in previous sections. No significant difference was observed for the three setups with varying sodium fluoride concentrations (0.005%, 0.01% and 0.02%). Each of the three setups showed better performance in stabilizing % HbA1c and preventing the increase of minor hemoglobins.

(5D) Soybean Trypsin Inhibitor (SBI)

A 4% SBI stock solution (manufactured and purified in house) was added to the cellular Hb A1c control product for stabilizing RBC. The final concentration of SBI was adjusted to 0.01% in the final product. Other commercial SBIs can also be utilized in this step, although the required concentration may be different. The addition of SBI did not change the performance of Hb A1c and other Hb fractions. However, controls containing SBI showed no or little hemolysis for more than 10 weeks and 10 months at room temperature and 6° C., respectively.

(5E) Additional Parameters

Additional parameters that may contribute to the performance and/or stability of the cellular Hb A1c controls include pH, osmolality, ciprofloxacin, bovine serum albumin, EDTA, alkali metal phosphate (di- and mono-basic).

Example 2

Preparing Normal (Level I) Cellular Hemoglobin A1c Controls Using Human RBC's

All normal RBC units were purchased from a commercial blood bank. There were time intervals of 3-14 days between blood drawing and unit arrival. The screening procedure, using 10 randomly selected RBC samples, was conducted immediately following the arrival of RBC units. Three qualified RBC units (A1c=5.0%, 5.2% and 5.3%) were identified using the Tosoh® A1c 2.2 Plus analyzer. The details of RBC units and screening procedure were described in section D 1.

A Level I A1c control (research pilot lot RPL #05004) was manufactured using the three qualified RBC units. The same general manufacturing flowchart (FIG. 1) was followed. The Level I Hb A1c control demonstrated a value of 5.8% for % A1c (Tosoh® HPLC).

Figure 6:
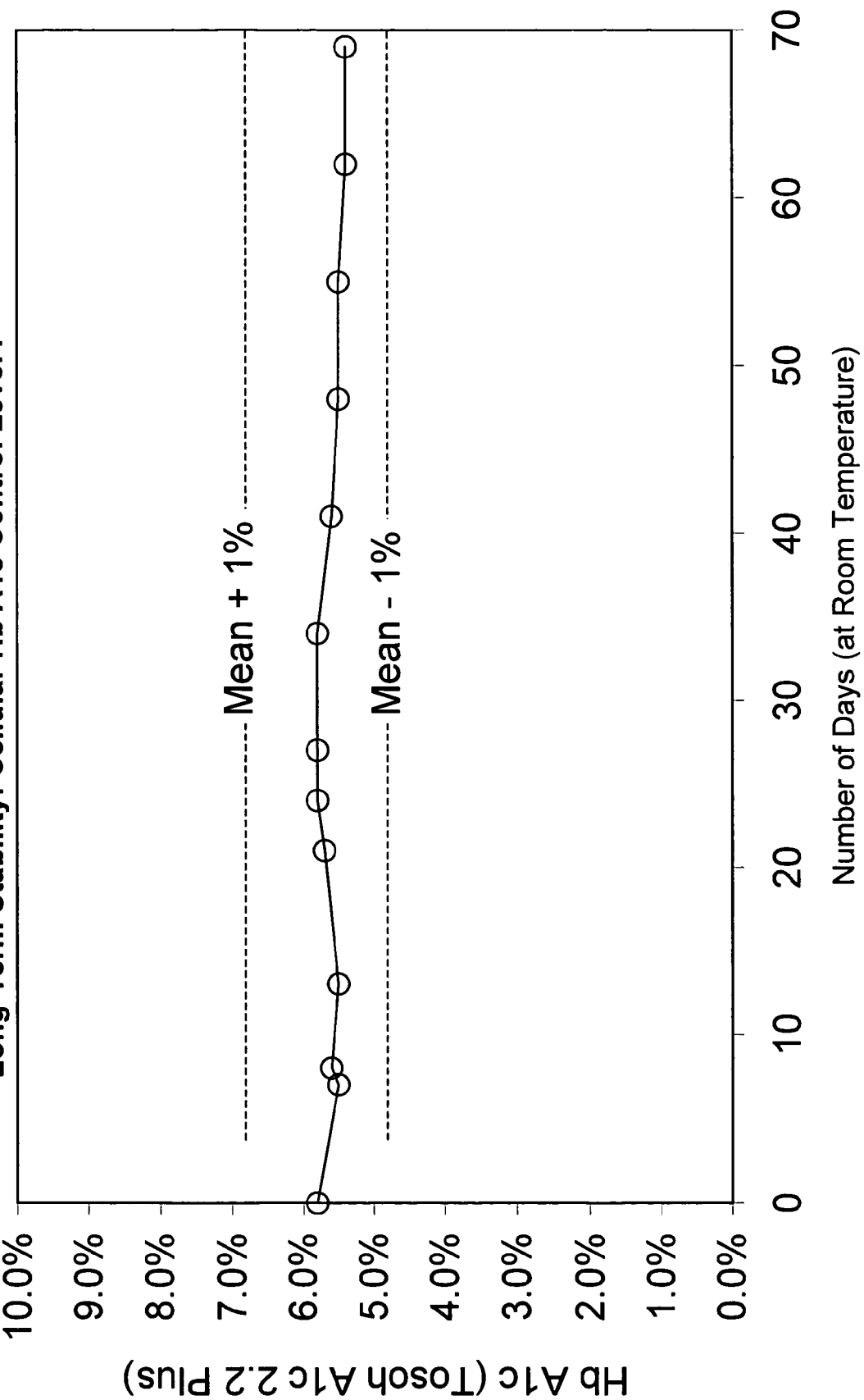
FIG. 6 shows the stability of the normal (Level I) cellular Hb A1c control.

Long-term stability (LTS) tests were conducted on a regular basis to demonstrate (1) that the normal Level I Hb A1c control varies no more than ±1% (percentage points), (2) that there is minimal change in HPLC chromatogram, and (3) that there is no or minimal RBC hemolysis, over the desired timeframe. One of the LTS studies was conducted at room temperature in order to accelerate the evaluation for approximately 10 weeks (FIG. 6). Only a minimal change in % Hb A1c (5.8% and 5.4% for Day 0 and Day 69, respectively) and very minor hemolysis were observed during this room temperature study, which indicated robust, desired stability for the Level I cellular Hb A1c control.

Samples of the Level I control (RPL #05004) were also evaluated by other Hb A1c testing systems. No significant discrepancy was reported for the values of % Hb A1c among all five systems (Table 8).

TABLE 8

Hb A1c Values of the Level I Control (Multiple Analyzers)

| Testing System | Methodology | Hb A1c |
| --- | --- | --- |
| Beckman ® CX/LX | Immunoassay | 5.1% (Day 71) |
| Bio-Rad ® Variant II | Ionic-Exchange HPLC | 6.6% (Day 65) |
| Cholestech GDX ® | Boronate Affinity | 5.2% (Day 71) |
| Tosoh ® A1c 2.2 Plus | Ionic-Exchange HPLC | 5.6% (Day 70) |
| Tosoh ® G7 | Ionic-Exchange HPLC | 6.0% (Day 65) |

The manufacturing parameters and their functions for preparing the Level I controls are similar to those described in EXAMPLE 1 and in previous sections, except for the concentration of glucose in the final diluent. The optimal concentration of glucose for the Level I A1c control is approximately 0.1%, which provides the best performance and stability for the. product.

Example 3

Development Of Abnormal High Hemoglobin A1c Control Via Slow Glycation At Low Temperature (1) Slow Synthesis of Hb A1c Using Normal RBC All normal RBC units were purchased from a commercial blood bank. Pooled samples from 10-15 randomly selected RBC units were first washed into a cell wash diluent as previously described in section C 1 and Table 2 and filtered by leukocyte removal filter. The ages of RBC's ranged from about 14 to about 28 days since blood drawing. The % Hb A1c value was 6.5% according to the Beckman Synchron CX® system.

The washed and filtered RBC samples were then incubated with a glycation diluent at a ratio of 1 to 2 ($V_{RBC}$:$V_{Diluent}$) at 6° C. The diluent contained about 3.15% glucose for increasing the rate of reaction and the yield of glycated products. The isotonic and pH neutral diluent also contained appropriate cell stabilizers, cell metabolites, buffers, antibiotics-antimicrobial agents and anti-fungal agents for stabilizing the RBC during the glycation reaction. The reaction was conducted at 6° C. to enhance the specificity of the glycation at the Hb A1c site (Val 1 of the Hb β chain).

The formulation of the glycation diluent is shown as follows.

TABLE 9

Example of Glycation Diluent for Synthesizing a Level II Control

| Components | Concentration (% w/V) |
| --- | --- |
| Methyl Paraben | 0.040% |
| PEG 20K | 0.300% |
| Inosine | 0.025% |
| Chloramphenicol | 0.015% |
| Neomycin Sulfate | 0.040% |
| EDTA (2Na$^+$) | 0.585% |
| Magnesium Gluconate | 0.325% |
| Na$_2$HPO$_4$ | 0.225% |
| NaOH | 0.070% |
| NaF | 0.005% |
| Glucose | 3.150% |
| pH | ~7.0 |
| Osmolality (mOsm) | 300 |

Figure 7:
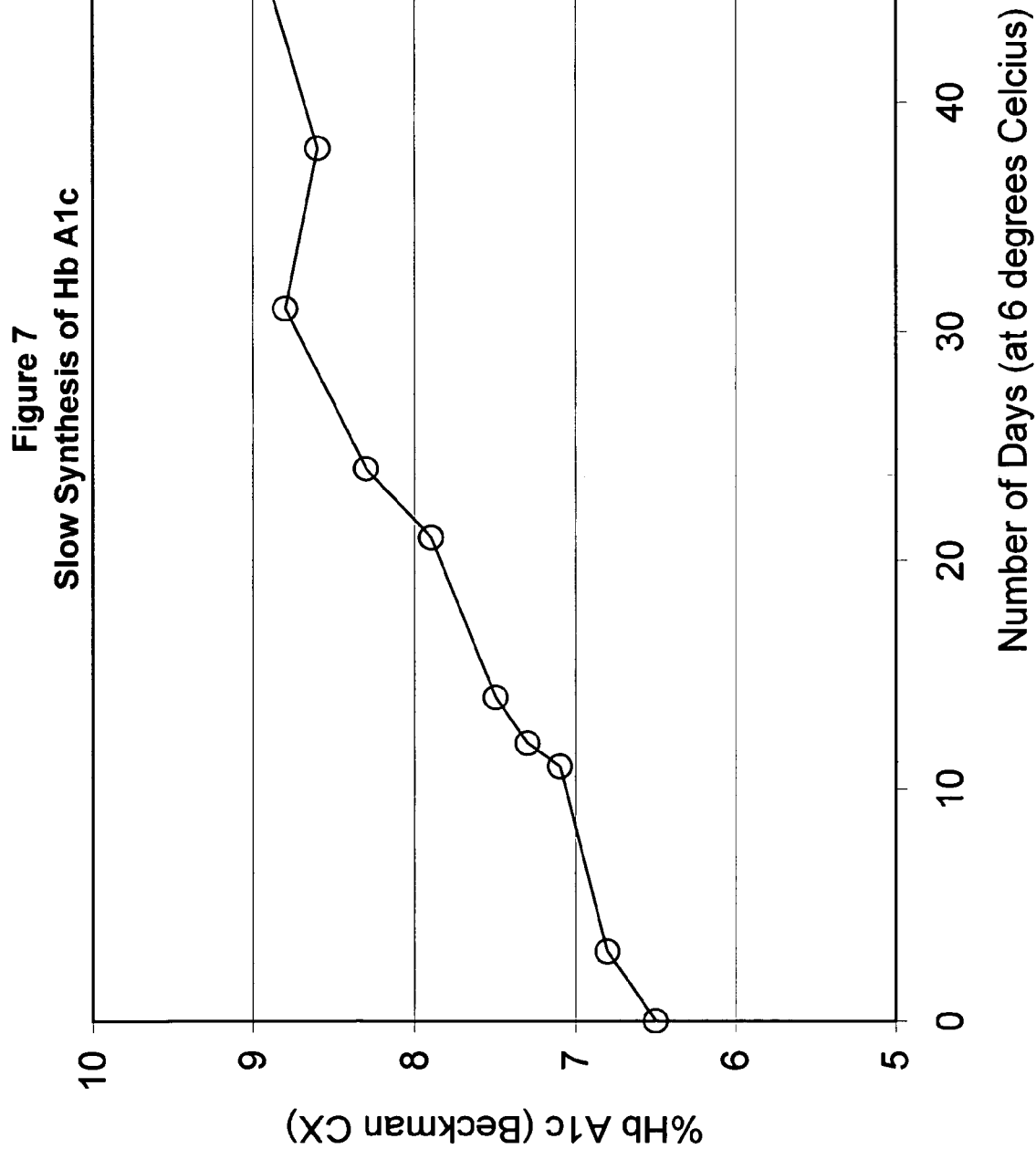
FIG. 7 shows the slow synthesis of Hb A1c in normal RBC's.

The synthesis of Hb A1c in the glycation reaction was monitored using the Beckman® system on a regular basis. FIG. 7 shows the Hb A1c synthesis process during the first 50 days of incubation at 6° C. A net growth of about 2.6% (percentage points) in % Hb A1c was detected, indicating an average growth rate of about 1% every 20 days. More than 99% of the RBC remained intact following the incubation, although higher concentration of glucose caused moderate amount of hemolysis.

(2) Preservation of the Synthesized Cellular Hemoglobin A1c Controls

The RBC's with glycated and unmodified Hb were furthered preserved by fixation and final washing after the incubation. The cell wash diluent (formulation in Table 2) was used to replace the hemolyzed supernatant before a fixation procedure by using 0.96 ml/L of a 25% glutaraldehyde solution for 6 hours at room temperature. The same cell wash diluent was used to wash; the RBC's three more times after the fixation to conclude the manufacturing of the synthesized control (referred to as RPL #03174). The samples of this control were tested using various Hb A1c testing systems with the following results: Hb A1c=8.8% (Beckman CX®), 8.7% (Tosoh® G7) and 8.8% (Beckman LX®).

The stability this synthesized control was determined using the Beckman Synchron CX® system. The samples from this synthesized control illustrated desirable stability (HbA1c=about 8.8% at Day 0, Hb A1c=about 7.5% at Day 154) and moderate hemolysis over a span of more than 150 days at 6° C.

Example 4

Manufacturing Abnormal High Cellular Glycohemoglobin (GHB) Controls Using Human RBC, Glucose and Cyanoborohydride.

In certain embodiments, the GHB/Hb A1c controls of the present invention were manufactured using post-filtered and pre-fixed RBC and a reaction solution containing higher concentrations of glucose and sodium cyanoborohydride. A flowchart with typical processing steps is shown below:

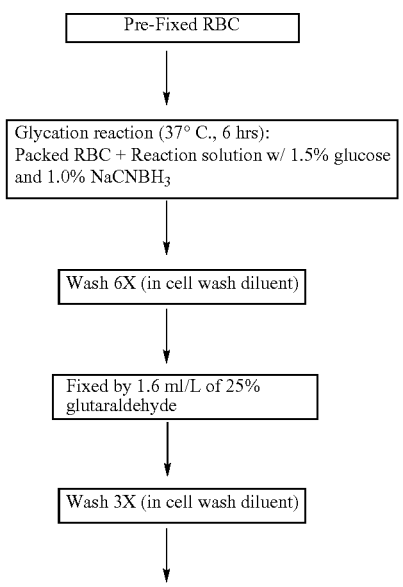

The glycation reaction solution was similar to the cell wash diluent described in Table 2, except it contained 1.5% glucose, 1.0% sodium cyanoborohydride (NaCNBH$_3$), and no potassium chloride (pH=7.0, osmolality=358 mOsm). The packed RBC and the reaction solution were mixed at 1:1 ratio (V:V) to initiate the glycation. The reaction was accelerated by incubating the reaction mixture at 37° C. for 6 hours. The RBCs with glycated hemoglobin were then stabilized by multiple washing and fixation procedures. The reductive glycation resulted in a high yield of final product (GHB=19.9%, A1c=14.6%). The values of % GHB were measured using the Helena Laboratories® Hb A1c kits and Cholestech GDX® designed by boronate affinity methodology. The values of Hb A1c were derived using an empirical formula: % Hb A1c=0.6846×% GHB+0.9733 (Little et al, Clin. Chem. 38, 2472-2478, 1992). Higher values of % GHB/% Hb A1c can be achieved by using higher concentrations of glucose and/or NaCNBH$_3$ or longer reaction time.

The finished product was placed at room temperature for accelerated stability test using the Cholestech GDX® system. The test showed very good stability for the glycated product: Hb A1c=about 14.6% at Day 0 and Hb A1c=about 14.9% at Day 49. The hemolysis of RBC was minor during the LTS test.

The cellular GHB/Hb A1c controls yielded by the reductive glycation are not favored for ionic-exchange HPLC or immunoassay testing methods.

All of the compositions and/or methods and/or processes and/or apparatus disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and/or apparatus and/or processes and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

What is claimed is:

1. A method for preparing a cellular hemoglobin A1c (Hb A1c) control comprising:
   (a) selecting a sample of red blood cells with at least one desired feature from a suitable subject;
   (b) washing the sample;
   (c) processing the washed sample to remove white blood cells;
   (d) preserving Hb A1c molecules in said sample, wherein said red blood cells are intact and said Hb A1c molecules are unmodified;
   (e) washing the sample of (d); and
   (f) adjusting the Hb A1c level to the predetermined level thereby producing a cellular Hb A1c control, wherein the level of Hb A1c of the control is substantially stabilized and detectable.

2. The method of claim 1, further comprising:
   (g) admixing the control of (f) in a suspension medium suitable for delivering said control to a suitable analytical instrument for analysis.

3. The method of claim 1, wherein said suitable subject is a mammal, an avian, or a reptile subject.

4. The method of claim 3, wherein said sample is obtained from human, bovine, or both human and bovine subjects.

5. The method of claim 3, wherein said sample is obtained from a diabetic subject.

6. The method of claim 1, wherein the Hb A1c level of the control is detectable using immunologic detection, ion exchange, or affinity chromatography.

7. The method of claim 1, wherein the Hb A1c level of the control is about 1-5%.

8. The method of claim 1, wherein the Hb A1c level of the control is greater than 5%.

9. The method of claim 1, wherein the Hb A1c level of the control is about 5-20%.

10. The method of claim 1, wherein said preserving comprises treating the cells with about 0.001-3% polyethylene glycol.

11. The method of claim 10, wherein said preserving comprises treating the cells with about 0.001-1% glucose.

12. The method of claim 1, wherein said preserving comprises fixing the red blood cells.

13. The method of claim 12, wherein said fixing comprises treating the cells with about 0.002-0.10% glutaraldehyde.

14. The method of claim 1, wherein said adjusting comprises maintaining pH at about 6-8.

15. The method of claim 1, further comprising after (c), incubating the red blood cells with about 3% glucose and about 0.5% NaCNBH$_3$ at room temperature.

16. The method of claim 1, further comprising after (c), incubating the red blood cells for at least about 50 days, at about 4-6° C., with a glycation solution which comprises:
    0.04% Methyl paraben;
    0.3% PEG 20K;
    0.025% Inosine;
    0.015% Chloramphenicol
    0.04% Neomycin Sulfate
    0.585% EDTA (2Na$^+$);
    0.325% Magnesium gluconate;
    0.225% Na$_2$HPO$_4$;
    0.07% NaOH;
    0.005% NaF; and
    3.15% Glucose;
wherein the osmolality of the glycation solution is adjusted to about 300±7 (mOsm) and pH is adjusted to about 7.0±0.1.

17. The method of claim 1, wherein said red blood cells are unlysed.

18. A cellular hematology control for Hb A1c comprising intact red blood cells having a predetermined level of Hb A1c, wherein the Hb A1c is unmodified, and the level is substantially stabilized.

19. The control of claim 18, wherein the red blood cells have a substantially stable Hb A1c content for at least about one month.

20. The control of claim 18, wherein the red blood cells have a substantially stable Hb A1c content for at least about three months.

21. The control of claim 18, wherein the Hb A1c level is about 1-5%.

22. The control of claim 18, wherein the Hb A1c level is greater than 5%.

23. The control of claim 18, wherein the Hb A1c level is about 5-20%.

24. The control of claim 18, wherein the predetermined level of Hb A1c is stabilized through adjusting pH of the control to about 6-8.

25. The control of claim 18, wherein the predetermined level of Hb A1c is stabilized through the addition of glucose at an amount of about 0.001-1%.

26. A method for determining the accuracy and reproducibility of the operation of an analytical instrument capable of measuring Hb A1c levels comprising
    (a) providing the cellular hematology control for Hb A1c of claim 18 in a known reference quantity;
    (b) determining the Hb A1c level in said control of (a) with said instrument; and
    (c) comparing the Hb A1c level obtained in (b) with said known reference quantity; wherein said comparing indicates the accuracy and reproducibility of the operation of said analytical instrument.

27. The control of claim 18, wherein said red blood cells are unlysed.

* * * * *

UNITED STATES PATENT AND TRADEMARK OFFICE
CERTIFICATE OF CORRECTION

| | |
|---|---|
| PATENT NO. | : 7,361,513 B2 |
| APPLICATION NO. | : 11/102378 |
| DATED | : April 22, 2008 |
| INVENTOR(S) | : Wayne L. Ryan and Jiong Wu |

It is certified that error appears in the above-identified patent and that said Letters Patent is hereby corrected as shown below:

Column 21, line 51, delete "0.00 1-3%" and insert --0.001-3%--.

Signed and Sealed this

Twenty-second Day of July, 2008

JON W. DUDAS
*Director of the United States Patent and Trademark Office*

UNITED STATES PATENT AND TRADEMARK OFFICE
CERTIFICATE OF CORRECTION

PATENT NO.        : 7,361,513 B2                                   Page 1 of 1
APPLICATION NO. : 11/102378
DATED             : April 22, 2008
INVENTOR(S)       : Wayne L. Ryan and Jiong Wu It is certified that error appears in the above-identified patent and that said Letters Patent is hereby corrected as shown below:

Column 21, line 51, delete "0.00 1-3%" and insert --0.001-3%--.

Signed and Sealed this

Fifth Day of August, 2008

JON W. DUDAS
*Director of the United States Patent and Trademark Office*